(12) United States Patent
Pardhasaradhi et al.

(10) Patent No.: US 6,555,695 B1
(45) Date of Patent: Apr. 29, 2003

(54) PROCESS FOR THE PREPARATION OF ETHYL 2,3-DIHYDROBENZO[1,4]DIOXIN-2-CARBOXYLATE

(75) Inventors: Malladi Pardhasaradhi, Andra Pradesh (IN); Gullapalli Kumaraswamy, Andra Pradesh (IN); Arun Kanti Das, Andra Pradesh (IN); Nivedita Jena, Andra Pradesh (IN); Chembumkulam Kamalakshyamma Snehalatha Nair, Andra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/077,494

(22) Filed: Feb. 14, 2002

(51) Int. Cl.[7] ............................................. C07D 319/14
(52) U.S. Cl. ...................................................... 549/362
(58) Field of Search .......................................... 549/362

(56) References Cited

U.S. PATENT DOCUMENTS 6,313,294 B1 * 11/2001 Chou et al. .................. 544/292

OTHER PUBLICATIONS

Fang et al, Tetrahedron:Asymmetry, 12, pp 2169–2174, 2001.*

* cited by examiner

Primary Examiner—Shailendra Kumar
(74) Attorney, Agent, or Firm—Abelman, Frayne, & Schwab

(57) ABSTRACT

The present invention relates to an improved process for the preparation of ethyl 2,3-dihydrobenzo[1,4]dioxin-2-carboxylate.

More particularly the present invention provides a process for the preparation of ethyl 2,3-dihydrobenzo[1,4]dioxin-2-carboxylate in hydrocarbon solvent in the presence of a base and catalytic amount of a phase transfer catalyst.

7 Claims, 1 Drawing Sheet

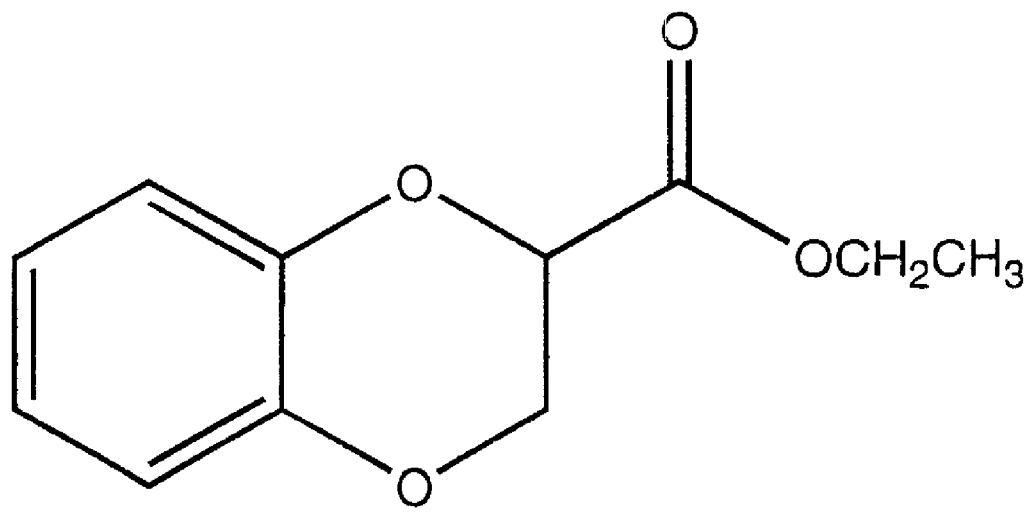
(±)
Formula - I

PROCESS FOR THE PREPARATION OF ETHYL 2,3-DIHYDROBENZO[1,4]DIOXIN-2-CARBOXYLATE

The present invention relates to a process for the preparation of ethyl 2,3-dihydrobenzo[1,4]dioxin-2-carboxylate.

Ethyl 2,3-dihydrobenzo[1,4]dioxin-2-carboxylate is an important starting material for the preparation of antihypertensive drug viz. Doxazosin. It is usually prepared by the condensation of N-(2,3-dihydrobenzo[1,4]dioxin-2-carbonyl) piperazine with 4-amino-2-chloro-6,7-dimethoxyquinazoline[J. Med. Chem, 1987, 30(1), 49]. N-(2,3-dihydrobenzo[1,4]dioxin-2-carbonyl) piperazine is a condensation product of ethyl 2,3-dihydrobenzo[1,4]dioxin-2-carboxylate and piperazine.

Ethyl 2,3-dihydrobenzo[1,4]dioxin-2-carboxylate was earlier prepared in 76% yield by condensation of catechol and 2,3-dibromopropionate in dry acetone in the presence of anhydrous potassium carbonate. The procedure requires the addition of potassium carbonate and dibromoester in four lots, over a period of 18 h. [J. Am. Chem. 80c. 1955, 77, 5374]. In the reported procedure, the formation of side product viz. ethyl-2-bromoacrylate (lachrymatic) is unavoidable and requires rigorous purification to isolate the desired product.

In view of the low yields and formation of side product (lachrymatic) in the preparation of ethyl 2,3-dihydrobenzo[1,4]dioxin-2-carboxylate, it is necessary to develop an alternative method in which higher yields of the desired product is obtained without the formation of lachrymatic side product.

The main objective of the present invention is to provide a process for the preparation of ethyl 2,3-dihydrobenzo[1,4]dioxin-2-carboxylate of the Formula-I see FIG. 1.

The another object of the present invention is to provide a process for the preparation of ethyl 2,3-dihydrobenzo[1,4]dioxin-2-carboxylate in hydrocarbon solvent in the presence of a base and catalytic amount of a phase transfer catalyst.

Accordingly, the present invention provides a process for the preparation of ethyl 2,3-dihydrobenzo[1,4]dioxin-2-carboxylate of the formula-1, which comprises reacting catechol with a base in a molar ratio of catechol to base in the range of 1:1 to 1:2 in a hydrocarbon solvent, removing the water by heating the reaction mixture at reflux temperature of the solvent, adding polyethylene glycol as phase transfer catalyst and 2,3-dibromopropionate to the above said reaction mixture and controlling the frothing by slowly adding alkali metal carbonate, stirring the resultant reaction mixture for a period of 3–10 hrs at a temperature ranging from 70–150° C., filtering the reaction mixture and washing the filtrate followed by concentration to obtain the desired product.

In an embodiment of the present invention the base used is selected from potassium hydroxide and potassium carbonate.

In an another embodiment the hydrocarbon solvent used is toluene In yet another embodiment the alkali metal carbonate used is selected from sodium carbonate and potassium carbonate.

The process of the present invention is detailed below:

In the improved process for the preparation of ethyl 2,3-dihydrobenzo[1,4]dioxin-2-carboxylate, a solution of catechol in a hydrocarbon solvent was reacted with base at a temperature preferably in the range of 100–120° C. for a period preferably in the range of 1–2 h using a Dean-Stark apparatus. To the above reaction mixture, polyethylene glycol and 2,3-dibromopropionate were added followed by slow addition of anhydrous potassium carbonate or sodium carbonate at the same temperature. It was refluxed for a period in the range of 2–6 h. The reaction mixture was filtered, filtrate washed with water, dried, and distilled to get the desired product.

The following examples are given by way of illustrations of the present invention and therefore should not be construed to limit the scope of the present invention.

Example 1 & 2 are Comparative Examples

Example 1

Into a 100 ml round bottom flask provided with a Dean-Stark apparatus, thermowell, dropping funnel and a magnetic bar, catechol (10 g, 0.09 moles), potassium carbonate (31.04 g, 0.226 moles) and toluene (50 ml) were taken at room temperature. It was heated to reflux to separate the water formed. 2,3-Dibromopropionate (25.74 g, 0.99 moles) was added over 45 min and refluxed for another 24 h. The solids were filtered and filtrate was washed with water. The organic layer was concentrated to give liquid residue. Product distilled at 105–115° C./0.2 mm (yield 3.78 g, 20%).

Example 2

Into a 100 ml round bottom flask provided with a Dean-Stark apparatus, thermowell dropping funnel and a magnetic bar, catechol (10 g , 0.09 moles) and sodium hydroxide (9 g, 0.226 moles) and toluene (50 ml) were taken at room temperature. It was heated to reflux to separate the water formed. 2,3-Dibromopropionate (25.74 g, 0.099 moles) was added over 45 min and refluxed for another 24 h. The solids were filtered and filtrate was washed with water. The organic layer was concentrated to give crude liquid residue. Product distilled at 105–115° C./0.2 mm, (yield 2.8 g, 15%).

Example 3

Into a 5 lit round bottom flask provided with a stirrer, Dean-Stark apparatus, dropping funnel and a thermowell, catechol (112 g, 1.0 mole); potassium hydroxide (56.11 g, 1.0 moles) and toluene (600 ml) were taken at room temperature. It was heated to reflux to separate out the water formed. Polyethylene glycol (5.5 g) and 2,3-dibromopropionate (286 g, 1.1 moles) were added over 45 min and refluxed. To the reaction mixture solid potassium carbonate (138 g, 1.0 mole) was added portion wise controlling the froathing. The reaction mixture was then stirred for 3 h to complete the reaction. The solids were filtered and filtrate was washed with water (2×200 ml). The organic layer was concentrated to give liquid residue. Product distilled at 105–115° C./0.2 mm (yield 180 g, 85%).

Example 4

Into a 100 ml round bottom flask provided with a Dean-Stark apparatus, dropping funnel, magnetic bar and a thermowell, catechol (10 g, 0.09 moles); potassium hydroxide (5 g, 0.09 moles) and toluene (50 ml) were taken at room temperature. It was heated to reflux to separate out the water formed. 2,3-Dibromopropionate (25.74 g, 0.09 moles) was added over 45 min and refluxed. To the reaction mixture solid potassium carbonate (12.4 g, 0.09 moles) was added portion wise controlling the froathing. The reaction mixture was then stirred for 3 h to complete the reaction. The solids were filtered and filtrate was washed with water (2×100 ml). The organic layer was concentrated to give liquid residue (yield 9.45 g, 50%).

The main advantages of the present invention are
1. It is a very convenient process in which toluene is used as solvent avoiding the usage of acetone, ether, etc., as solvents.
2. This process facilitates the formation of ethyl 2,3-dihydrobenzo[1,4]dioxin-2-carboxylate in 85% yield in short reaction time of 4–6 h.

What is claimed is:

1. A process for the preparation of ethyl 2,3-dihydrobenzo[1,4]dioxin-2-carboxylate of Formula I,

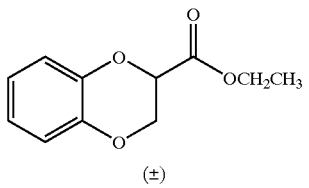

Formula I (±)

which comprises:
 a) reacting catechol with a base in a molar ratio of catechol to base in the range of about 1:1 to about 1:2 in a hydrocarbon solvent;
 b) removing the water by heating the reaction mixture at the reflux temperature of the solvent;
 c) adding polyethylene glycol as a phase transfer catalyst and 2,3-dibromopropionate to the reaction mixture and controlling the frothing by slowly adding alkali metal carbonate;
 d) stirring the resultant reaction mixture for a period of about 3 to about 10 hours at a temperature ranging from about 70 to about 150° C.; and
 e) filtering the reaction mixture and washing the filtrate followed by concentrating to obtain the desired product.

2. The process according to claim 1, wherein the base used is selected from potassium hydroxide and potassium carbonate.

3. The process according to claim 1, wherein the hydrocarbon solvent used is toluene.

4. The process according to claim 1, wherein the alkali metal carbonate used is selected from sodium carbonate and potassium carbonate.

5. The process according to claim 2, wherein the hydrocarbon solvent used is toluene.

6. The process according to claim 2, wherein the alkali metal carbonate used is selected from sodium carbonate and potassium carbonate.

7. The process according to claim 3, wherein the alkali metal carbonate used is selected from sodium carbonate and potassium carbonate.

* * * * *